(12) United States Patent
Jaroszeski et al.

(10) Patent No.: US 11,318,304 B2
(45) Date of Patent: May 3, 2022

(54) SYSTEM AND METHOD FOR ELECTROPORATION CONTROLLED BY ELECTRICAL IMPEDANCE MEASUREMENTS

(71) Applicants: Douglas Walter Brown, Northumberland, PA (US); University of South Florida, Tampa, FL (US)

(72) Inventors: Mark Jeffrey Jaroszeski, Wesley Chapel, FL (US); Timothy Fawcett, Seffner, FL (US); Richard Jason Connolly, Riverview, FL (US); Andrew M. Hoff, Tampa, FL (US); Reginald Morley Atkins, Riverview, FL (US); Douglas Walter Brown, Northumberland, PA (US); Richard A. Gilbert, Tampa, FL (US)

(73) Assignee: University of South Florida, Tampa, FL (US)

( * ) Notice: Subject to any disclaimer, the term of this patent is extended or adjusted under 35 U.S.C. 154(b) by 343 days.

(21) Appl. No.: 15/720,322

(22) Filed: Sep. 29, 2017

(65) Prior Publication Data
US 2018/0036529 A1    Feb. 8, 2018

Related U.S. Application Data

(63) Continuation of application No. PCT/US2016/025263, filed on Mar. 31, 2016.
(Continued)

(51) Int. Cl.
*A61N 1/32* (2006.01)
*C12M 1/42* (2006.01)

(52) U.S. Cl.
CPC ............ *A61N 1/326* (2013.01); *C12M 35/02* (2013.01); *A61N 1/327* (2013.01)

(58) Field of Classification Search
CPC .... A61N 1/0412; A61N 1/0476; A61N 1/327; A61N 1/326; A61N 1/0575;
(Continued)

(56) References Cited

U.S. PATENT DOCUMENTS

| | | | |
|---|---|---|---|
| 6,387,671 B1 * | 5/2002 | Rubinsky | A61B 5/0536 435/173.1 |
| 2006/0121446 A1 * | 6/2006 | Abassi | G01N 33/48728 435/4 |
| 2008/0091135 A1 * | 4/2008 | Draghia-Akli | A61N 1/327 604/20 |
| 2010/0023004 A1 | 1/2010 | Francischelli et al. | |
| 2015/0330927 A1 * | 11/2015 | Lee | G01N 27/023 435/6.12 |

OTHER PUBLICATIONS

Gomez, Lina, "Impedance Measurements as a Means to Improve the Biological Response of Gene Electrotransfer", 2015, University of South Florida Scholar Commons, p. 1-41 (Year: 2015).*
(Continued)

*Primary Examiner* — Kevin C Sirmons
*Assistant Examiner* — Alexandra Lalonde
(74) *Attorney, Agent, or Firm* — Molly L. Sauter; Smith & Hopen, P.A.

(57) ABSTRACT

The present invention provides a system and a method for measuring an impedance of one or more target cells before and after an electroporation protocol has been applied to the one or more target cells. A result of the impedance measurement provides a feedback control that can be implemented during and/or after the electroporation protocol to customize an electrical treatment for a particular target cell or cellular tissue.

10 Claims, 3 Drawing Sheets

Related U.S. Application Data

(60) Provisional application No. 62/140,960, filed on Mar. 31, 2015.

(58) Field of Classification Search
CPC ...... A61N 2001/083; A61N 1/32; A61N 1/18; A61N 1/20; A61N 1/30; A61N 1/303; A61N 1/306; A61N 1/325; A61N 1/0408; A61N 1/0404; A61N 1/04; A61N 1/02; A61N 1/0428; A61N 1/0568; A61N 1/08; A61N 1/36031; A61N 1/36135; A61N 1/36139; A61N 1/3614; A61N 1/36521; A61B 2018/00875; C12M 35/02; A61K 41/0047; A61M 2230/65; A61M 37/00; A61M 2037/0007; A61M 2205/50; A61M 2205/0233; A61M 2205/0272; A61M 2205/054; A61M 2205/3327
See application file for complete search history.

(56) References Cited

OTHER PUBLICATIONS

Gomez. Impedance Measurements as a Means to Improve the Biological Response of Gene Electrotransfer. University os South Florida Scholar Commons: Graduate Theses and Dissertations. 2015: 1-47.

International Search Report and Written Opinion for PCT/US2016/025263 (filing date: Mar. 31, 2016) dated Aug. 12, 2016; Applicant: University of South Florida.

International Preliminary Report on Patentability for PCT/US2016/025263 (filing date: Mar. 31, 2016) with a priority date of Mar. 31, 2015; Applicant: University of South Florida.

* cited by examiner

SYSTEM AND METHOD FOR ELECTROPORATION CONTROLLED BY ELECTRICAL IMPEDANCE MEASUREMENTS

CROSS-REFERENCE TO RELATED APPLICATIONS

This application is a continuation of and claims priority to International Patent Application No. PCT/US2016/025263, entitled "System and Method for Electroporation Controlled by Electrical Impedance Measurements", filed Mar. 31, 2016 by the same inventors, which claims priority to U.S. Provisional Patent Application No. 62/140,960, entitled "System and Method for Electroporation Controlled by Electrical Impedance Measurements", having a filing date of Mar. 31, 2015, the entirety of which is hereby incorporated by reference.

STATEMENT OF GOVERNMENT INTEREST

This invention was made with government support under Grant Number R21 AR061136 awarded by the National Institutes of Health. The government has certain rights in the invention.

BACKGROUND OF THE INVENTION

In the past 15 years, in vivo electroporation for DNA delivery has been under investigation in preclinical trials for many types of normal tissues and tumors. A large variety of normal tissues have been treated with electroporation for DNA delivery; the primary targets being skin and muscle. Additionally, a large number of different tumors have been treated, including: melanoma, fibrosarcoma, gliomas, and hepatocellular carcinomas.

Electroporation technology has progressed from the first electroporation clinical trials in the 1990's for drug delivery to about 85 active, recruiting, or completed clinical trials, based on the www.clinicaltrials.gov database information. The technologies are known in the art for delivering both DNA and drugs to a variety of tissues including skin, muscle, and tumor tissues. Thus, it appears that electroporation technology is progressing and will have long-lasting clinical application.

There are many variables that effect electroporation. These include tissue type, electrode type, subject-to-subject (human or animal) variation, as well as human factors relating to the manual placement of electrodes and the injection of therapeutic molecules. Differences in tissue architecture and/or chemical composition may effectively create unique biological environments from subject to subject that may respond differently to identical electroporation parameters. In order to identify the required electroporation parameters, painstakingly derived empirical electroporation parameters have been the norm for the field since its inception. The derivation of these parameters involves performing multiple series of experiments to investigate the most appropriate electrode to be used to deliver the electric pulses to the subject and the proper applied electric field strength, number of pulses, duration of each pulse, shape of each pulse, and interval between pulses (for multiple pulse protocols). These empirically derived electroporation parameters are what yield the desired biological response for a particular delivery situation, on average. Unfortunately, empirically derived parameters cannot compensate for differences that are encountered when applying the same treatment to multiple different subjects (animals or patients).

Accordingly, what is needed in the art is a system and method for performing electroporation that is adaptable for the effective treatment of multiple subjects.

SUMMARY OF INVENTION

The system and method of the present invention improves the manner in which electroporation is practiced. The present invention diverges from the traditional means of applying electroporation that simply applies pulses with a fixed set of electrical parameters, which does not compensate for the variations that are inevitable from animal to animal, tissue to tissue, or person to person. As such, the present invention refines the skilled art of applying electroporation to a more quantitative procedure.

In accordance with one embodiment of the present invention, a method for performing electroporation of one more target cells is provided. The method may include, introducing one or more molecules to be delivered to one or more target cells, measuring a first impedance of the one or more target cells, applying a first electroporation protocol to the one or more target cells, measuring a second impedance of the one more or target cells following the application of the first electroporation protocol, comparing the first impedance and the second impedance of the one or more target cells and determining if the application of the first electroporation protocol has been effective in delivering the one or more molecules to the one or more target cells based upon the comparison of the first impedance and the second impedance of the one or more target cells.

The method may further include, applying a second electroporation protocol to the one or more target cells if it is determined that the application of the first electroporation protocol has not been effective in delivering the one or more molecules to the one or more target cells based upon the comparison of the first impedance and the second impedance of the one or more target cells.

In one embodiment, the first electroporation protocol and the second electroporation protocol may be the same protocol. In another embodiment, the first electroporation protocol and the second electroporation protocol may be different protocols.

In various embodiments, the method of the present invention may be applied to one or more target cells both in vitro and in vivo.

In an additional embodiment of the present invention, a device for the delivery of electroporation and measurement of impedance of one or more target cells is provided. In various embodiments, the device may include, an electrode array comprising a plurality of individually addressable electrodes, a plurality of relays, one of each of the plurality of relays coupled to one individually addressable electrode of the electrode array, an electric field generator coupled to the plurality of relays, an impedance measurement system coupled to the plurality of relays and a controller coupled to the plurality of relays, the controller for selectively coupling the electric field generator or the impedance measurement system to the electrode array. The electric field generator may be a high-voltage electric field generator and the impedance measurement system may be a low-voltage impedance spectroscope.

Accordingly, the present invention provides a system and method for performing electroporation that is adaptable for the effective treatment of multiple subjects utilizing quantifiable, real-time, impedance measurements of the cells/tissue being treated.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

The present invention provide a system and method for measuring changes in the electrical impedance of cells/tissues resulting from electroporation treatment and using the measured changes as a real-time measure that indicates if cells have been sufficiently electrically treated to yield a desired biological response a molecule delivered to the cells/tissue. One of the advantages of the present invention is that it can compensate for variations in the electroporation parameters that can differ from patient-to-patient, thereby providing the ability to customize the electroporation treatment for each individual patient.

The present invention comprises an integrated device comprising both a system for applying the electrical pulses necessary to achieve electroporation within cells/tissue and a system for measuring impedance of the cells/tissue. The measured impedance can be used as a feedback control for the electroporation protocol that can be implemented during and/or after the application of each electrical pulse to customize the electrical treatment for a particular cells/tissue. In the present invention, the it is shown that the measured impedance is reduced in the tissue following electropulsing and the impedance of the tissue can also be rapidly measure, in real-time. Additionally, the system to measure the impedance of the tissue utilizes many of the same components of the system required for performing electroporation, thereby allowing for the design of an integrated device effective for performing both impedance measurement and electroporation delivery.

In support of the system and method of the present invention, impedance changes due to irreversible electroporation have been measured in rat liver, following a theoretical study that proposed the feasibility of using impedance to monitor electroporation in vivo. A follow-up investigation indicated that it is possible to distinguish between reversible and irreversible electroporation in murine fibrosarcomas in vivo. Impedance changes resulting from electroporation in rat lung tissue (ex vivo or in vitro) have been described. An additional study used tissue phantoms, ex vivo tissue and in vivo tissues, to suggest that measured impedance may indicate an electroporated state and could, theoretically, be used as an indicator of electroporation. While none of these studies delivered molecules to tissues with electroporation, their results strongly suggest that impedance provides a measurable change that occurs as a result of electroporation.

In a particular embodiment of the present invention, a computer controlled impedance analyzer for applying both DC pulses for electroporation of a target cells/tissue and for measuring the impedance of the target cells/tissue, before and after an electroporation pulse is administered, is provided. The electroporation pulsing and impedance measurement system is illustrated with reference to FIG. 1A and FIG. 1B.

Figure 1B:
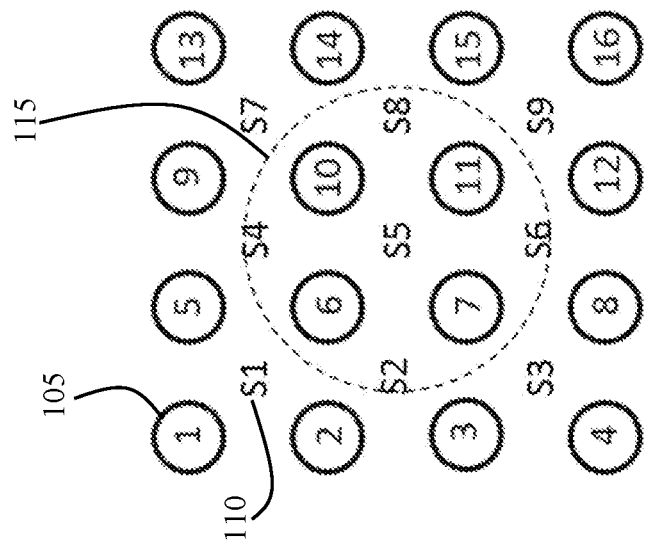
FIG. 1B illustrates an electrode configuration for an electroporation application and impedance measurement device, in accordance with an embodiment of the present invention.
Figure 1A:
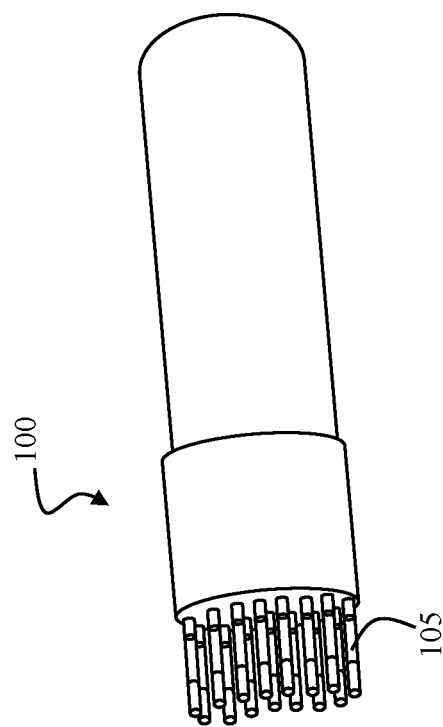
FIG. 1A illustrates an electroporation application and impedance measurement device, in accordance with an embodiment of the present invention.

With reference to FIG. 1A and FIG. 1B, in a particular embodiment, the electric field delivery instrumentation hardware 100 includes an electrode array comprising sixteen electrodes 105 and thirty-two (32) isolated solid state relays coupled to the sixteen electrodes 105, wherein the 32 solid state relays are controlled by a data acquisition and control module. Sixteen of the relays are connected to a positive terminal, while the other sixteen relays are connected to a ground terminal of a high voltage power supply. An impedance spectroscope and an electric field generator are coupled to the solid state relays. The impedance spectroscope may include an I/P card for generating a multi-frequency sine analog voltage reference signal buffered by a unity gain high-bandwidth amplifier rated to drive capacitive loads. A pair of instrumentation amplifiers may be coupled to the I/O card of the impedance spectroscope to measure a differential voltage across, and current flowing through, a tissue sample and to buffer the measured results. In a particular embodiment, the sampling rate for both the reference signal generation and the voltage/current measurements may be about 1 MHz. In this embodiment, the electric field generation and impedance measurement instrumentation 100 are combined into a single composite instrument that permits impedance spectra to be obtained before and/or after electric field pulses have been applied, using the same electrode array. This arrangement assures that the electric field and the impedance measurement occur in the same tissue region. In this embodiment, the solid state relays are used to rapidly connect and disconnect the high voltage pulse delivery instrument and the low voltage impedance measurement portion of the instrument. The solid state relays, the high voltage pulse delivery system and the low voltage impedance measurement system of the hardware are coupled to a computer processing system running associated software for controlling the instrument and for processing the measured impedance data. The software may control the creation of, and distribution of, electroporation pulses through the electrode array. The software may also control the measurement of the impedance of the tissue, both before and after the electroporation pulses have been applied. Comparison of impedance values after each successive electroporation pulse may be used as criteria for either continuing the electroporation pulsing or discontinuing the pulsing, depending upon how much the impedance had dropped.

Pulsed electric fields and impedance measurements can be made with the direct contact multielectrode array (MEA) applicator illustrated in FIG. 1A and FIG. 1B. In this particular embodiment, the application comprises sixteen gold-plated 0.54 mm diameter flat bottom electrodes that are spaced 2.5 mm apart, center to center, creating a square geometry with a side length of 8.0 mm. The array created nine 2.5 mm by 2.5 mm square spaces between electrodes, with each spacing referred to as a sector of treated tissue. Each electrode in the application may be spring loaded, which allows the tips to conform to differences in animal skin topology, ensuring that the electrodes maintain good contact with the tissue of interest. As shown in FIG. 1B, sixteen electrodes 105 are configured into 9 sections 110, each section comprising four electrodes. Electric pulsing and post-pulse impedance measurements may be conducting utilizing the various defined sectors of electrodes. The dashed line 115 is an indicator of the relative size of an intradermally injected bolus of DNA centered within electrodes 6, 7, 10 and 11.

The embodiment illustrated in FIG. 1A and FIG. 1B is exemplary in nature, and as sush, various other electrode configurations are within the scope of the present invention.

As indicated above, the MEA applicator is used for both the application of the electric fields to induce electroporation and gene electro transfer and for impedance measurements of the tissue. In an exemplary embodiment, the impedance spectroscope generates a 1V amplitude continuous sine wave excitation signal containing linearly spaced frequencies from 10 Hz to 100 kHz with a total duration of 25 ms. In a particular embodiment, the 25 ms duration signal begins 50 ms after the last pulse in each of the sectors. Once the voltage and current waveforms are collected by the impedance spectroscope, the Fourier transform of both waveforms can be calculated using the Fast Fourier Transform (FFT) algorithm, as is commonly known in the art.

Figure 2:
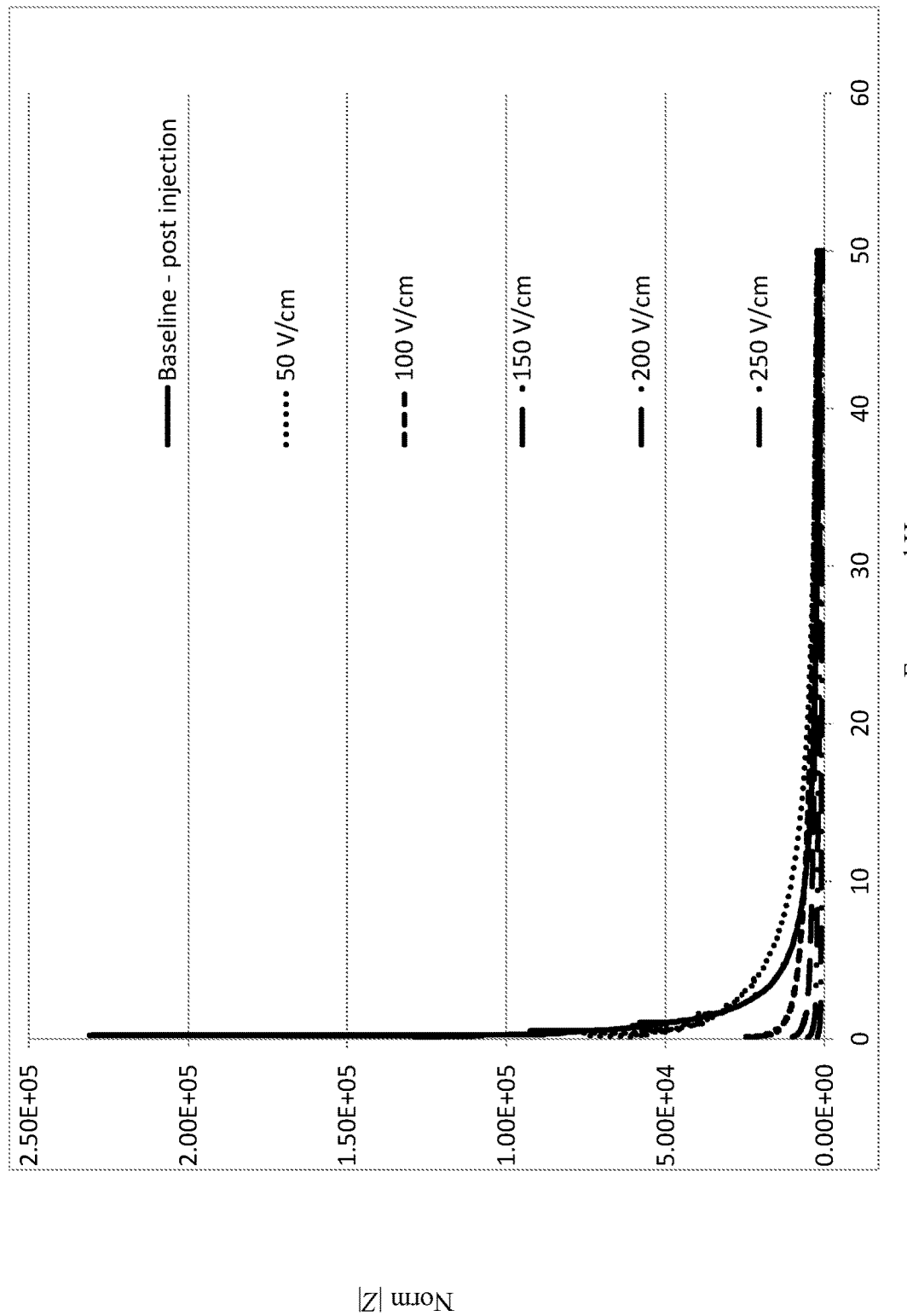
FIG. 2 is a graphical representation of post electroporation impedance spectra from murine skin that has first been injected with plasmid DNA solution, in accordance with an embodiment of the present invention.

In an experimental embodiment, the treatment device of the present invention was used to measure the impedance of murine skin that had been injected with the plasmid DNA encoding luciferase. The impedance, over a wide range of frequencies was measured, after pulsing animal tissue with pulses ranging from 50 V/cm to 250 V/cm. The resulting data is shown with reference to FIG. 2. In this exemplary embodiment, for each electrical treatment, 4 DC electric pulses that were 150 ms in duration were applied with an interval of 500 ms between electric pulses. As illustrated in FIG. 2, the range of frequencies where the largest change in impedance occurred was between 0 and about 10 kHz.

Following the results shown in FIG. 2, in an experimental embodiment, a frequency range of 1 kHz to 3 kHz was used as a frequency range with which to control the application of pulses to the skin in real-time to determine if increased delivery and subsequent expression would result when compared to delivering 4 pulses only (the standard electroporation method). In an experimental embodiment, DNA was administered intradermally as a bolus injection containing 50 μL of luciferase pDNA at a concentration of 2 mg/ml, resulting in a total of 100 μg/injection. In the experimental embodiment, eleven different treatment groups were established to illustrate the relationship between the delivery of luciferase plasmid to murine skin via electroporation and the subsequent impedance measurements of the tissue. The first treatment group was an untreated control group which received neither an applied electric field nor a pDNA injection. The second group received pDNA only (DO). The remaining nine treatment groups received pDNA followed by electric pulses. Impedance measurements were taken before, during and after electrical treatment in the five treatment groups receiving pDNA followed by electric pulses (DEI). The nine treatment groups varied only in the applied electric fields, which were 100V/cm, 150V/cm and 200V/cm.

Figure 3:
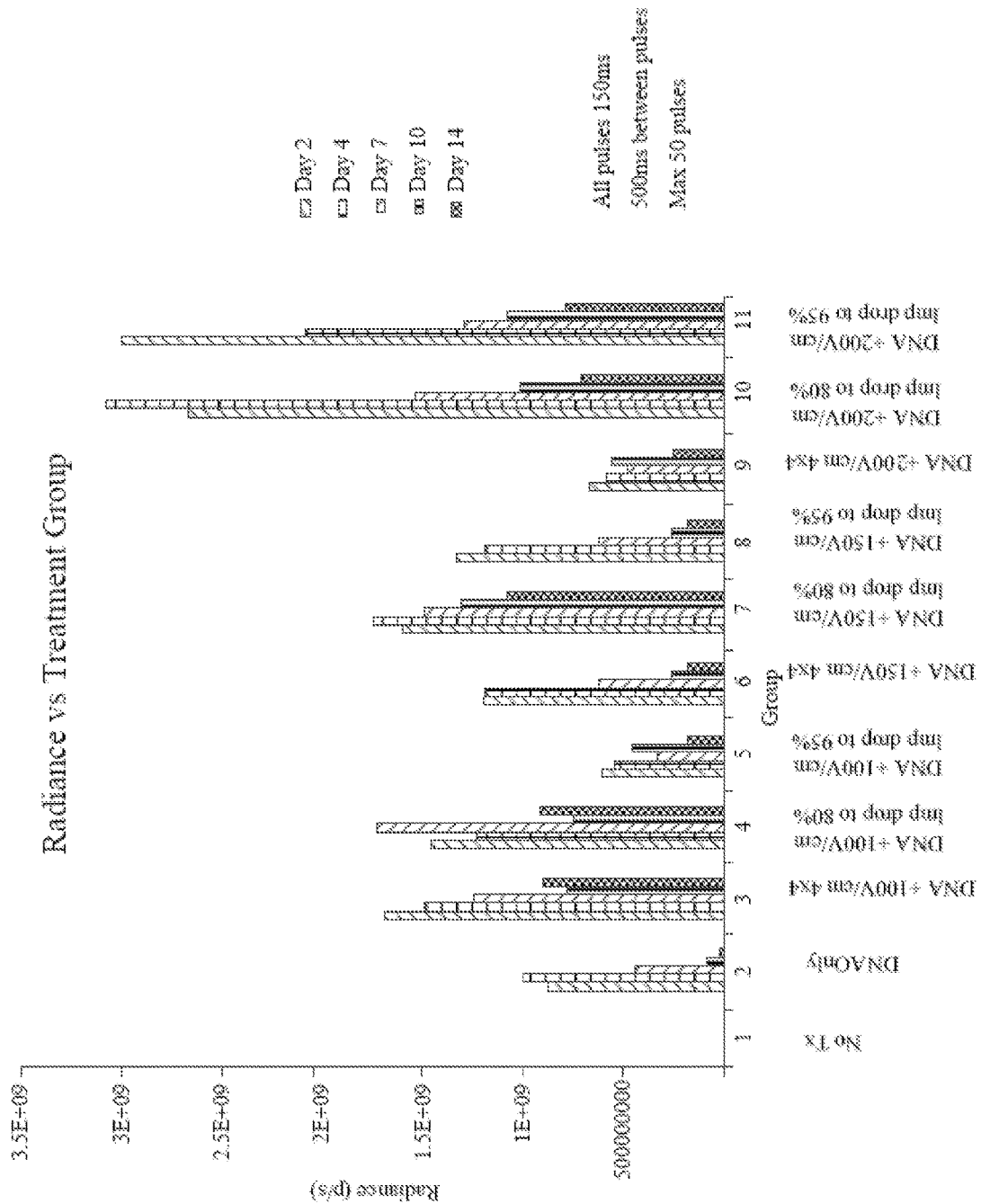
FIG. 3 is a graphical representation of luciferase expression results from impedance feedback based pulsing, in accordance with an embodiment of the present invention.

For this experiment, pulses were applied to skin in succession, as described above. After each pulse, impedance measurements were made and the mean norm (Z) was calculated and compared to the norm of the post injection, but pre-pulsed, norm. Pulsing was stopped when the mean norm of the impedance measurement in the 1 kHz to 3 kHz range had been reduced by either 80% or 95%, when compared to the pre-pulsed mean norm. The experiment was conducted using electric field strengths of 100 V/cm, 150 V/cm, and 200 V/cm. Transfection was quantified from luminescence produced by the oxidation of luciferin by the expressed reporter gene luciferase. Animals were placed into an imaging system and radiance (photons) was measured over a 10 second exposure time. This procedure was used to collect luminescence data 2, 4, 7, 10 and 14 days post treatment. The results of the experimental embodiment are illustrated with reference to FIG. 3. The results indicate that modulating the number of pulses using real-time impedance feedback can result in increased biological expression of the delivered foreign DNA. These results are not likely limited to modulating the number of pulses, but parameters such as the field strength (voltage) and pulse duration can also be modulated. Also, while the feedback system of the present invention is operated in the frequency domain, measurements can also be made in the time domain, which can also yield impedance data that can be used for feedback.

Therefore, one significant aspect of the present invention is the demonstration of tissue impedance drops that are associated with successful DNA delivery by electroporation. Another significant aspect is that the tissue impedance drops are directly correlated with biological response in the same animals. Therefore, data can be interpreted with respect to how much of an impedance drop is needed to maximize/optimize the desired biological response. This data can be used to circumvent the empirical determination of electroporation parameters for DNA delivery, to assure that the required amount of energy is applied for delivery, to avoid tissue damage by applying too many pulses and to avoid under pulsing which leads to a lower biological response.

In effect, the use of impedance measurements and feedback control, in accordance with the present invention, results in a customized electrical treatment each time electroporation is applied, ensuring a successful delivery and biological response. This novel quantitative approach to applying electroporation will transform the current state of the art of electroporation from a skillfully applied technique to one that can successfully be used by anyone in the field.

As electroporation is moved into the clinic, it is even more critical that each treatment be successful. The present invention may provide a personalized system/method that can compensate for all the variables that can influence electrical treatment such as person to person variation, skin thickness differences in different body locations, and different electrode configurations. The present invention is applicable to other tissue types by adaptation, just as electroporation is adaptable to different tissues.

The present invention may be embodied on various computing platforms that perform actions responsive to software-based instructions. Instructions stored on a computer readable medium may be utilized to enable the invention. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C#, C++ or the like and conventional procedural programming languages, such as the "C" programming language or similar programming languages.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall there between.

What is claimed is:

1. A device for delivery of electroporation and measurement of impedance of one or more target cells, the device comprising:
   an electrode array comprising a plurality of electrodes;
   a pulsing and impedance measurement system coupled to the electrode array, the pulsing and impedance measurement system comprising:
      an impedance measurement system configured to measure a first impedance of the one or more target cells following introduction of one or more molecules to be delivered to the one or more target cells;
      an electric field generator configured to apply an electroporation protocol to the one or more target cells after the first impedance of the one or more target cells is measured, wherein the electroporation protocol comprises one or more adjustable parameters;
      the impedance measurement system further configured to measure a second impedance of the one or more target cells following the application of the electroporation protocol to the one or more target cells;
      a computer processing system running associated software, wherein the computer processing system is configured to compare the first impedance and the second impedance of the one or more target cells to determine if the application of the electroporation protocol has been effective in delivering the one or more molecules to the one or more target cells based upon the comparison of the first impedance and the second impedance of the one or more target cells;
      the computer processing system further configured to provide feedback to the electric field generator to adjust the one or more adjustable parameters of the electroporation protocol based upon the comparison of the first impedance and the second impedance of the one or more target cells; and
      the electric field generator further configured to apply a subsequent electroporation protocol to the one or more target cells, wherein the subsequent electroporation protocol comprises the adjusted one or more adjustable parameters.

2. The device of claim 1, wherein the plurality of electrodes are individually addressable electrodes.

3. The device of claim 2, wherein the individually addressable electrodes are individually addressable needle electrodes.

4. The device of claim 1, wherein the pulsing and impedance measurement system comprises:
   a plurality of relays, one of each of the plurality of relays coupled to one electrode of the electrode array;
   wherein the electric field generator is coupled to the plurality of relays;
   wherein the impedance measurement system is coupled to the plurality of relays; and
   wherein a controller is coupled to the plurality of relays.

5. The device of claim 4, wherein the controller is configured to selectively couple the electric field generator or the impedance measurement system to the plurality of electrodes of the electrode array using one or more relays of the plurality of relays, wherein;
   the controller is configured to couple the impedance measurement system to the electrode array using one or more relays of the plurality of relays to measure the first impedance of the one or more target cells following the introduction of the one or more molecules to be delivered to the one or more target cells;
   the controller is configured to couple the electric field generator to the electrode array using one or more relays of the plurality of relays to apply the electroporation protocol to the one or more target cells; and
   the controller is configured to couple the impedance measurement system to the electrode array using one or more relays of the plurality of relays to measure the second impedance of the one or more target cells following the application of the electroporation protocol to the one or more target cells.

6. The device of claim 5, wherein the controller is configured to continue to couple the one or more relays of the plurality of relays between the electric field generator and the electrode array to apply the electroporation protocol to the one or more target cells and is configured to continue to couple the one or more relays of the plurality of relays between the impedance measurement system and the electrode array to measure the second impedance of the one or more target cells until a comparison of the first impedance and the second impedance of the one or more target cells indicates that the second impedance is lower than the first impedance by a predetermined amount.

7. The device of claim 4, wherein the electric field generator is configured to generate a voltage of between 50 V/cm and 250 V/cm.

8. The device of claim 1, wherein the impedance measurement system is a low-voltage impedance spectroscope to generate a 1V amplitude continuous sine wave excitation signal containing linearly spaced frequencies from 10 Hz to 100 kHz.

9. The device of claim 1, wherein the one or more adjustable parameters of the electroporation protocol are selected from an electrical pulse field strength, a number of electrical pulses and an electrical pulse duration.

10. The device of claim 1, wherein determining if the application of the electroporation protocol has been effective in delivering the one or more molecules to the one or more target cells based upon the comparison of the first impedance and the second impedance of the one or more target cells further comprises, determining if the second impedance is lower than the first impedance by a predetermined amount.

* * * * *